(12) United States Patent
Carrascosa

(10) Patent No.: US 9,357,907 B2
(45) Date of Patent: Jun. 7, 2016

(54) DEVICE FOR PERFORMING EXAMINATION THROUGH THE UTERINE CAVITY

(76) Inventor: Patricia Marina Carrascosa, Buenos Aires (AR)

( * ) Notice: Subject to any disclaimer, the term of this patent is extended or adjusted under 35 U.S.C. 154(b) by 469 days.

(21) Appl. No.: 13/125,894

(22) PCT Filed: Apr. 6, 2010

(86) PCT No.: PCT/ES2010/070214
§ 371 (c)(1),
(2), (4) Date: Jun. 29, 2012

(87) PCT Pub. No.: WO2011/051517
PCT Pub. Date: May 5, 2011

(65) Prior Publication Data
US 2012/0265058 A1    Oct. 18, 2012

(30) Foreign Application Priority Data
Oct. 27, 2009    (AR) .................................. 090104134

(51) Int. Cl.
*A61B 1/32* (2006.01)
*A61B 1/303* (2006.01)
*A61B 17/02* (2006.01)
*A61B 17/42* (2006.01)

(52) U.S. Cl.
CPC .............. *A61B 1/303* (2013.01); *A61B 17/0206* (2013.01); *A61B 17/42* (2013.01)

(58) Field of Classification Search
CPC ..................................... A61B 1/32; A61B 1/06
USPC .................................................... 600/220, 221
See application file for complete search history.

(56) References Cited

U.S. PATENT DOCUMENTS

| | | | |
|---|---|---|---|
| 3,037,505 A | 6/1962 | Walden et al. | |
| 3,320,948 A | 5/1967 | Martin | |
| 4,585,438 A | 4/1986 | Makler | |
| 8,696,561 B2 * | 4/2014 | Fenster et al. | ................ 600/221 |
| 2005/0085699 A1 | 4/2005 | Weiss | |

FOREIGN PATENT DOCUMENTS

GB     2391815 A     2/2004

OTHER PUBLICATIONS

International Search Report issued May 27, 2010 for PCT Application No. PCT/ES2010/070214.

\* cited by examiner

*Primary Examiner* — David Isabella
*Assistant Examiner* — Christine Nelson
(74) *Attorney, Agent, or Firm* — Locke Lord LLP; Daniel J. Fiorello; Howard M. Gitten

(57) ABSTRACT

A device for performing examination through the uterine cavity, preferably to carry out a computed tomography virtual hysterosalpingography, by the use of a speculum and a cannula or probe, wherein the device comprises a support for centering in the speculum and the probe is retained in a central end of the support to guarantee the centering of the probe within the cervix and the holding of the probe in the desired position during the test.

9 Claims, 4 Drawing Sheets

DEVICE FOR PERFORMING EXAMINATION THROUGH THE UTERINE CAVITY

CROSS-REFERENCE TO RELATED APPLICATIONS

This Application is a U.S. National Stage application under 35 U.S.C. 371 of International Application No. PCT/ES2010/070214 which claims priority to Argentine Application AR090104134, filed Oct. 27, 2009, each of which is hereby incorporated by reference herein in its entirety.

BACKGROUND OF THE INVENTION

1. Field of the Invention

The current invention is related to the field of medical devices used for medical exams related to the feminine genital organ and, more precisely, reference is made to a device to perform an examination called Multidetector computed tomography virtual hysterosalpingography that allows for the use of digital technology to take images and avoid traumatic manipulations to which the patient is submitted with radiologic technologies and associated devices that are currently being used.

2. Description of the Prior Art

Before starting off with the description of the devices and systems that are currently known in the art and used to assist while performing medical exams such as the one related to the current invention, more particularly, Computed Tomography Virtual Hysterosalpingography, also known as Computed Tomography Histogram; Computed Tomography Uterosalpingography; Computed Tomography Uterotubography, it is necessary to at least generally reference this examination which will facilitate understanding of the object and content of the invention.

The computed tomography hysterosalpingography is an examination that allows for the tomographic visualization of the uterine cavity and the tubes, which is performed via the introduction of a radiopaque contrast liquid, diluted to 80% through the uterine cervix. This test is particularly indicated for sterility and fertility studies, in other words all disorders that lead to lack of conception and failure of pregnancies. This visualization provides information about the uterine and tubal cavities, such as the size, shape, position and potential pathologies. The examination also allows us to determine whether the uterine tubes are obstructed. The big difference with the conventional format (conventional or traditional hysterosalpingography) is that the virtual examination by computed tomography provides bidimensional, tridimensional and virtual endoscopic information which allows for a more precise diagnose. It does not only assess the uterine cavity but also the wall and external morphology of the uterus as well as visualize the pelvis as a whole, hereby allowing for the identification of adnexal and extra-gynaecological pathologies that may be associated.

In order to perform the conventional hysterosalpingography procedure, the patient is placed in the gynaecological position and before asepsis of the perineum a sufficiently lubricated speculum is placed to gain access to the cervix, after which the speculum is fixed in its position. Next, the vagina is cleaned and disinfected and a Risolia metallic cannula which in turn has a metal olive at its extremity which puts pressure on the external cervical orifice in order to occlude it and avoid reflux of the contrast fluid which is introduced a couple of millimeters inside the cervix. The cervix is taken at 12 o'clock from the exterior with a metallic forceps (Erina forceps) that was specifically designed for this purpose. The forceps and the cannula are immediately and simultaneously tractioned to deploy the uterine cervix in order to take the images. In other words, the uterine cervix, which generally contains curves that do not allow for complete or clear images to be taken, is straightened. This item is particularly important for the trauma that is caused to the patient, using a forceps that grabs the cervix, not only because it causes discomfort, in the best of cases, but also because it can be painful and causes small wounds with corresponding bleeding and/or additional infections.

Once the cervix has been tractioned with the cannula in its interior, the contrast liquid is injected and the area is irradiated to take the radiological images. Generally, oblique and lateral images are taken in order to show the entire uterus, the tubes and the passage of the contrast fluid to the peritoneum. This implies that the patient must change position during the taking of the images. Afterwards the instruments are withdrawn, the area is evacuated and sedatives and sometimes antibiotics are recommended.

This procedure is deficient because of at least three significant disadvantages. One is that it is considerably time-consuming, at times up to 40 minutes, which only increase the traumatic experience for the patient. Another disadvantage is that the cannula, grasper, connections of the cannula with the source of the liquid and the manual handles for the injection of the liquid into the uterus should be held and manipulated by professional staff that must stay with the patient almost constantly, whereby they are almost always exposed to X-radiation. Finally, the other disadvantage is that it only provides information about the interior of the organs (cervix, uterus and tubes), a "luminogram", without giving information about the wall or their external morphology.

Considering the current state of the art available for the realization of medical exams such as the one mentioned previously, it would be very convenient to have a new technology to perform these exams in a shorter time span, without the need for continued assistance of medical personnel and without causing (or reducing to a minimum) any traumatic manipulations on the patient's body parts, while at the same time obtaining clearer images, with increased anatomic detail and with the additional possibility of using digital imagery techniques by means of modern instruments that use a reduced dose of X-radiation.

SUMMARY OF THE INVENTION

It is therefore a purpose of the current invention to provide a new, simple device that can easily and quickly be assembled and operated for the preparation of a patient for medical examination of the uterine cavity which does not require traction of the cervix as it can be applied with digital imagery technology such as multi-slice tomographs and other modern imagery systems.

It is a further object of the present invention to provide a device for performing examination through the uterine cavity, preferably to carry out a computed tomography virtual hysterosalpingography, using a speculum and a cannula or probe, wherein the device comprises a support for centering the speculum and the probe is retained in a central end of the support to guarantee the centering of the probe within the cervix and the holding of the probe in the desired position during the test.

It is still another object of the present invention to provide a device for performing examination through the uterine cavity, such as the exam known as computed tomography virtual hysterosalpingography, of the type that is carried out by introducing an injecting cannula that delivers a fluid into the uterus, with the help of a vaginal speculum arranged into the vagina to facilitate access to the cervix of the patient, the speculum comprising at least two valves joined together by a mechanism for opening/closing said valves, wherein the device comprises a support in at least one of said valves, with said support having at least one arm extending towards a central longitudinal axis of the speculum and ending in a holding end, and said cannula is regulably and removably retained in said holding end of said arm of the support, the cannula having a distal end with a sealing plug.

BRIEF DESCRIPTION OF THE DRAWINGS

For better clarity and comprehension, the present invention is illustrated by way of example in the following drawings wherein.

DESCRIPTION OF THE PREFERRED EMBODIMENTS

Figure 1:
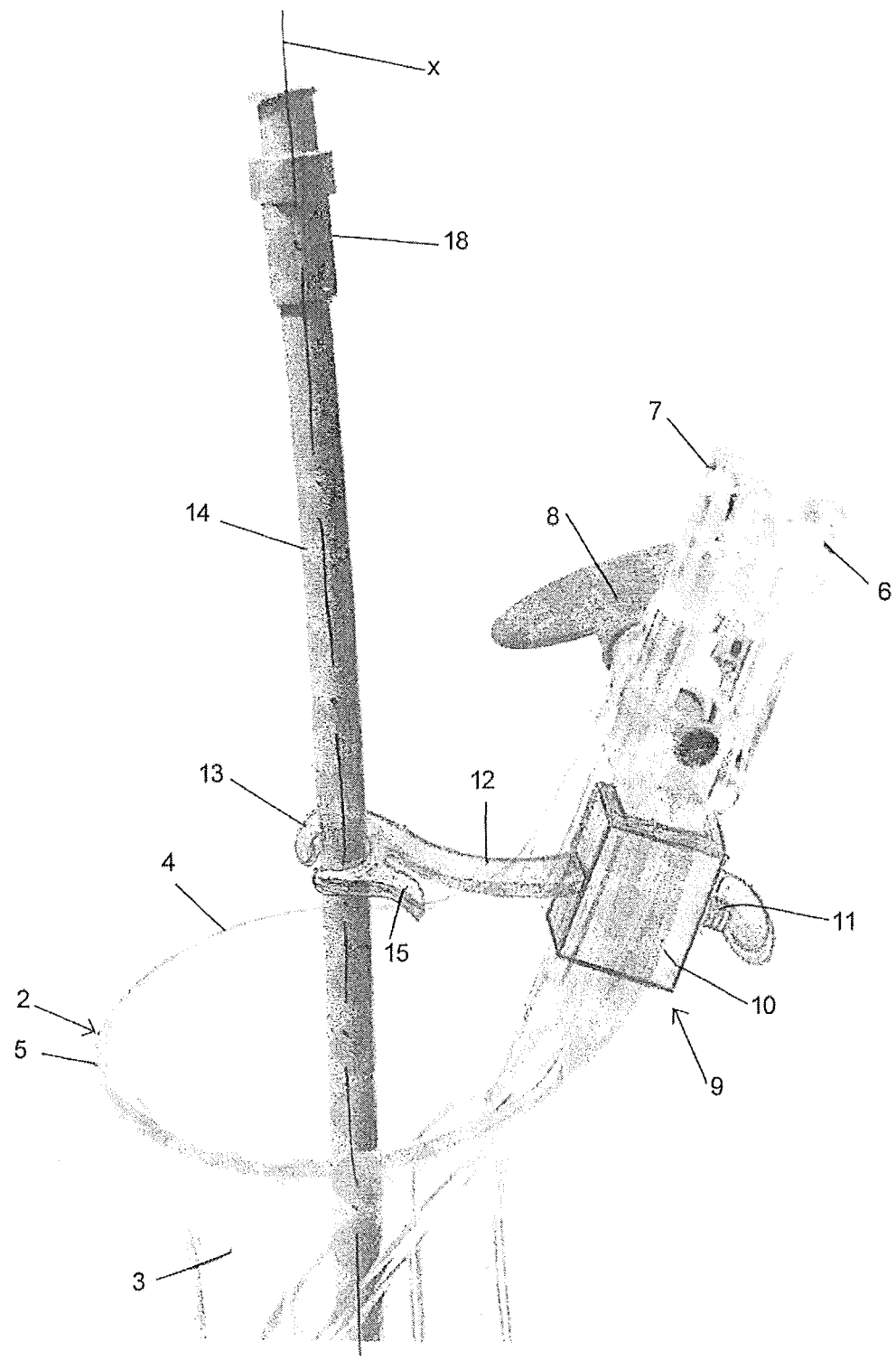
FIG. 1 shows a rear perspective of the device in agreement with one of the preferred embodiments of the invention.
Figure 2:
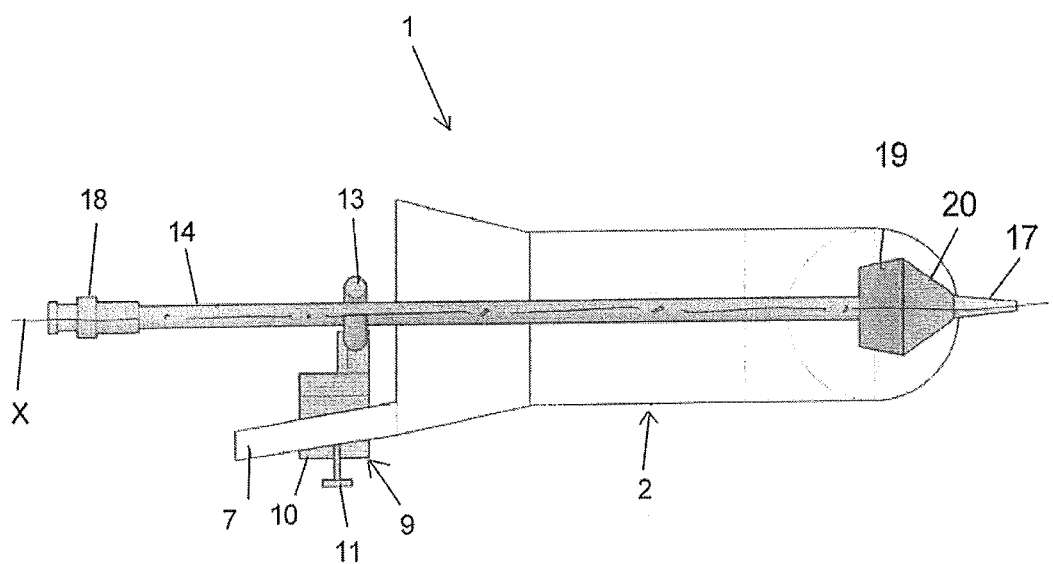
FIG. 2 shows an elevated side-view of the device that is the subject of the invention.

By looking at the figures we can deduce that the invention comprises a device for performing an examination through the uterine cavity, and more preferably to perform a procedure corresponding to an examination known as computed tomography virtual hysterosalpingography, which has been referenced above in this description. The device, indicated with the general reference number 1 in the drawings, is composed by a speculum (2) that can comprise two or more valves and that preferably is a speculum composed by two valves 3 and 4, opposed by their sides, as indicated with reference number 5. The speculum 2 can be a known speculum, whose valves 3 and 4 are joined together by an opening/closing mechanism with an adjustable hinge. The valve opening/closing mechanism comprises two arms 6, 7 that are connected by means of an internal hinge (which has not been illustrated) and an adjustment screw 8 which is screwed onto at least one of said arms of the speculum. By handling the screw 8 it is possible to bring the arms 6, 7 closer together or further apart and consequently closing or opening valves 3, 4. The material used for the speculum should preferably be transparent and fit for medical use.

In agreement with the invention, the speculum will be provided with a support which will be fixed to the speculum in any convenient way, removable or not, but preferably fixed to one of the valves and more preferably fixed to one of the arms 6 of the valves of the speculum such as is shown in the preferred embodiment. The support 9 has a fixation end for fixing it to the speculum and said fixation end 10 has a "C" shape that encircles said arm 6 of the opening/closing mechanism, the fixation end 10 having a fixing screw 11 to firmly, and preferably in a removable manner, fixate the support 9 to the speculum. From said fixation end 10 of the support an arm 12 is projected which runs along the central longitudinal axis X of the speculum and ends in a holding end 13 which will be located, if possible, in the central axis X or as close to it as possible. This will of course depend on several factors, such as for example the anatomy of the patient, the working conditions, etc.

Figure 3:
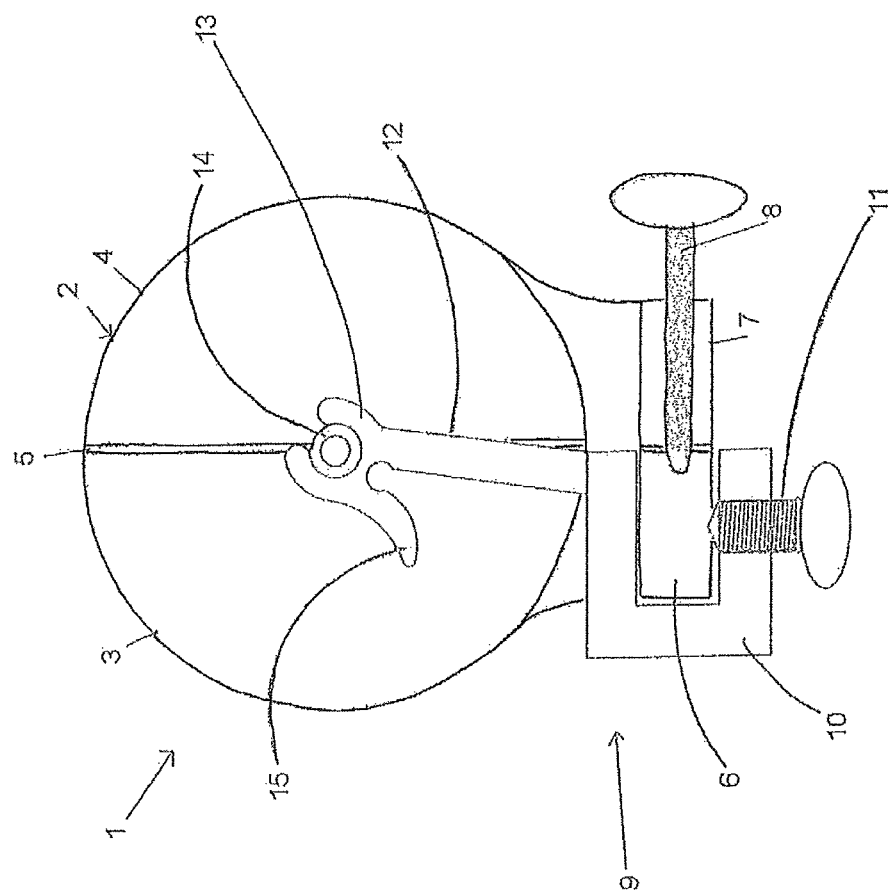
FIG. 3 shows a partial side-section viewed from the proximal or latter extremity of the device that is the subject of the invention.

The holding end can present any convenient shape to momentarily and firmly house one or more probes or cannulas 14, which will be referenced below, but preferably the holding end 13 has an open ring shape, as can be appreciated in the FIGS. 1 and 3, with a trigger 15 for the elastic opening of the ring. Effectively, the support 9 will be made from a sufficiently rigid material in order to firmly maintain its position and fix the position of the probe 14, but also sufficiently elastic as to allow the annular deformation of the holding end 13 in such a way that the cannula fits within the split ring end. Polypropylene or high-density polyethylene are recommendable materials but other well-known materials from the medical field, preferably transparent ones, can also be used. Of course the shape of the split ring can be modified in function of the amount of probes used and their shape.

Figure 4:
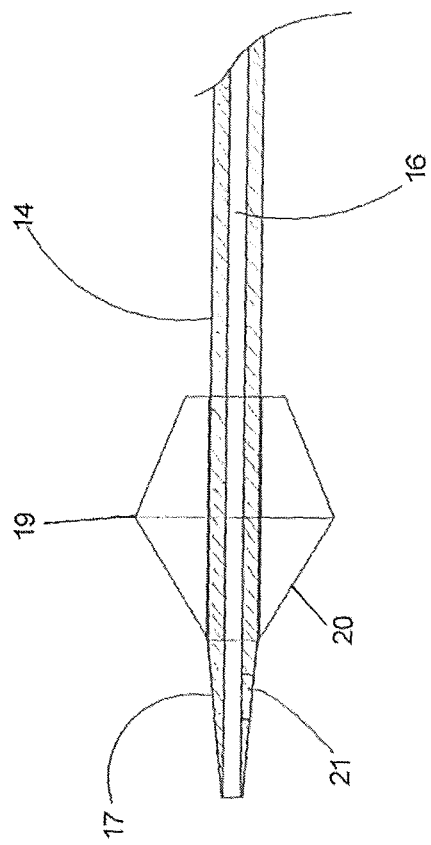
FIG. 4 shows an elevated and partial side-view of the distal end of the probe or cannula of the device that is the subject of the invention.

The probe or cannula 14, better illustrated in the section in FIG. 4, has a circulation channel 16 for the contrast liquid which can have color or not, which is used for the medical examination and is injected into the uterus. To easily penetrate within the cervix, the cannula has a spindle-shaped distal end 17, which has been finished in order to avoid damage when it is introduced into the cervix. Furthermore, the holding end 17 will be provided with lateral orifices 21, in any convenient way, be they circular, elongated, etc. in order to facilitate the exit of the contrast liquid. On its other end, the cannula has a proximal connection end 18 that allows us to connect, preferably by screwing the probe or cannula 14 onto a tube for supplying said fluid which in turn will form part of the fluid provider assembly with an appropriate pump for that purpose.

The distal end 17 of the cannula is provided with an elastic sealing plug 19, such as for example silicone or butyl gum, and has a conical leading profile that is extended towards the cervix. Said conical profile 20 forms a 45° angle although other angles are also possible depending on the anatomy of the patient. Once the end 17 of the cannula is inside the cervix and the contrast liquid has been injected, the conical surface 20 will be in contact with the external surface of the cervix and will seal off any losses as a result of liquid reflux. This conical surface can also be combined with a ringed profile to favor liquid retention.

By using the device of the invention, the exam procedure is performed much quicker and much less traumatically than with the known procedures as it does not use graspers to straighten the uterus. This is no longer necessary as more advanced and less dangerous examination techniques of the patient can be used such as the multislice computed tomography which scans the area to be examined using axial images with high anatomic detail that allow for the posterior generation of views from different angles without the need for the patient to be moved from her original position. On the other hand, the examination is done much more quickly and practically for the intervening medical personnel, as the installed device can be left inside the patient during the test, which is very short, without the need of attention from a doctor, whereby he is not exposed to radiation.

The assembly of the device is quick and easy and consists of housing the support into the speculum using the fixation end 9 and its fixation by means of quick adjustment of the screw 8. Afterwards, the speculum is placed into the vagina and the cannula is mounted onto the holding end 13 of the arm 12. The cannula can be assembled before inserting the speculum into the vagina. The position of the speculum can be fixed even if this has not been done yet and the cannula is moved until the end 17 is placed within the cervix and until the conical surface 20 of the plug 19 rests against the cervix.

The cannula, previously connected or not to the liquid-providing tube, can be easily assembled onto the end 13 with one hand by pulling the trigger or lever 15 and there it will remain firmly in place so the cannula will be held firmly within the cervix, sustained and centered by the arm 12 and pushed towards the cervix by this same elastic arm. The arm can be bent outwards while the cannula is retained, hereby obtaining an elastic pressure that pushes the cannula towards the uterus. Once this position has been reached, the fluid delivery assembly is operated to inject the liquid into the uterus and to start the examination, quickly, without trauma and by means of a very easy operation.

The invention claimed is:

1. A device for performing examination through the uterine cavity by introducing an injecting cannula that delivers a fluid into the uterus, the device comprising:
   a vaginal speculum including at least two valves joined together by a mechanism for opening/closing said valves, the speculum being designed to be arranged into the vagina to facilitate access to the uterine neck of a patient, wherein said mechanism for opening/closing the valves includes two arms articulably connected to each other by an opening/closing regulating screw;
   a support having a "C" shaped fixation end for removably and directly fixing to at least one of said arms of the mechanism, with the "C" shaped fixation end encircling and being removably fixed to said at least one arm of the mechanism by a fixing screw;
   a resilient arm extending from the "C" shaped fixation end towards a central longitudinal axis of the speculum and having a free holding end capable of being placed close or in the central longitudinal axis of the speculum and resiliently moving relative to said "C" shaped fixation end; and
   a sealing plug in a distal end of an injecting cannula, with the cannula being regulably and removably retained in said holding end of said resilient arm of the support.

2. The device of claim 1, wherein said holding end of the resilient arm of the support has an open ring-shape with a trigger for elastic opening of a ring.

3. The device of claim 2, wherein said sealing plug has a conical leading profile extended towards the uterine neck.

4. The device of claim 3, wherein said conical leading profile forms a 45° angle with respect to a longitudinal axis of the conical leading profile.

5. The device of claim 1, wherein said cannula has a connecting proximal end for connection to a tube for supplying said fluid and a distal end that is a tapered distal end.

6. The device of claim 1, wherein said plug is made of a resilient material.

7. The device of claim 6, wherein said plug material is selected from silicone and butyl rubber.

8. The device of claim 1, wherein said support is made of a transparent material.

9. The device of claim 1, wherein the fixing screw is outside the speculum valves and spaced apart from the central longitudinal axis of the speculum.

\* \* \* \* \*